(12) United States Patent
Jansen et al.

(10) Patent No.: US 9,012,187 B2
(45) Date of Patent: Apr. 21, 2015

(54) DICARBOXYLIC ACID PRODUCTION BY FERMENTATION AT LOW PH

(75) Inventors: Mickel Leonardus August Jansen, The Hague (NL); René Verwaal, Nootdorp (NL)

(73) Assignee: DSM IP Assets B.V., Heerlen (NL)

( * ) Notice: Subject to any disclaimer, the term of this patent is extended or adjusted under 35 U.S.C. 154(b) by 102 days.

(21) Appl. No.: 13/003,217

(22) PCT Filed: May 20, 2009

(86) PCT No.: PCT/EP2009/056181
§ 371 (c)(1),
(2), (4) Date: Jan. 7, 2011

(87) PCT Pub. No.: WO2010/003728
PCT Pub. Date: Jan. 14, 2010

(65) Prior Publication Data
US 2011/0229945 A1    Sep. 22, 2011

(30) Foreign Application Priority Data

Jul. 8, 2008  (EP) ..................................... 08159891

(51) Int. Cl.
*C12P 1/00* (2006.01)
*C12P 7/46* (2006.01)

(52) U.S. Cl.
CPC ........................ *C12P 7/46* (2013.01)

(58) Field of Classification Search
None
See application file for complete search history.

(56) References Cited

U.S. PATENT DOCUMENTS

2003/0228671 A1    12/2003  Hause et al.

FOREIGN PATENT DOCUMENTS

| CN | 1688703 A | 10/2005 |
|---|---|---|
| WO | WO 00/71738 | 11/2000 |
| WO | 03102152 A2 | 12/2003 |
| WO | WO 2007/106524 | 9/2007 |
| WO | WO 2008/144626 | 11/2008 |
| WO | WO 2009/011974 | 1/2009 |

OTHER PUBLICATIONS

Yévenes et al. (Expression of the *Trypanosoma brucei* phosphoenolpyruvate carboxykinase gene in *Saccharomyces cerevisiae*, Biochimie 82 (2000) 123-127).*
Luttik et al. (J. Biol. Chem. 1998, 273:24529-24534).*
International Search Report for PCT/EP2009/056181, mailed Dec. 14, 2009.
Written Opinion of the International Searching Authority for PCT/EP2009/056181, mailed Dec. 14, 2009.
Zelle, R. et al., "Malic Acid Production by *Saccharomyces cerevisiae*: Engineering of Pyruvate Carboxylation, Oxaloacetate Reduction, and Malate Export", Applied and Environmental Microbiology, vol. 74, No. 9, (May 1, 2008), pp. 2766-2777.
Abbott, D. et al., "Metabolic Engineering of *Saccharomyces cerevisiae* for Production of Carboxylic Acids: Current Status and Challenges", FEMS Yeast Research, vol. 9, No. 8, (Dec. 2009), pp. 1123-1136.

* cited by examiner

*Primary Examiner* — Suzanne M Noakes
*Assistant Examiner* — Jae W Lee
(74) *Attorney, Agent, or Firm* — Miles & Stockbridge PC

(57) ABSTRACT

The present invention relates to a process for the production of a dicarboxylic acid. The process comprises fermenting a yeast in the presence of a carbohydrate-containing substrate and low amounts of oxygen at a pH value at which at least 50% of the dicarboxylic acid is in the acid form. The process of the present invention allows for high yields of the dicarboxylic acid product and is more cost-effective than existing processes in which the salt is produced which during recovery has to be converted to the acid. It also leads to a simpler and more convenient downstream processing.

14 Claims, 1 Drawing Sheet

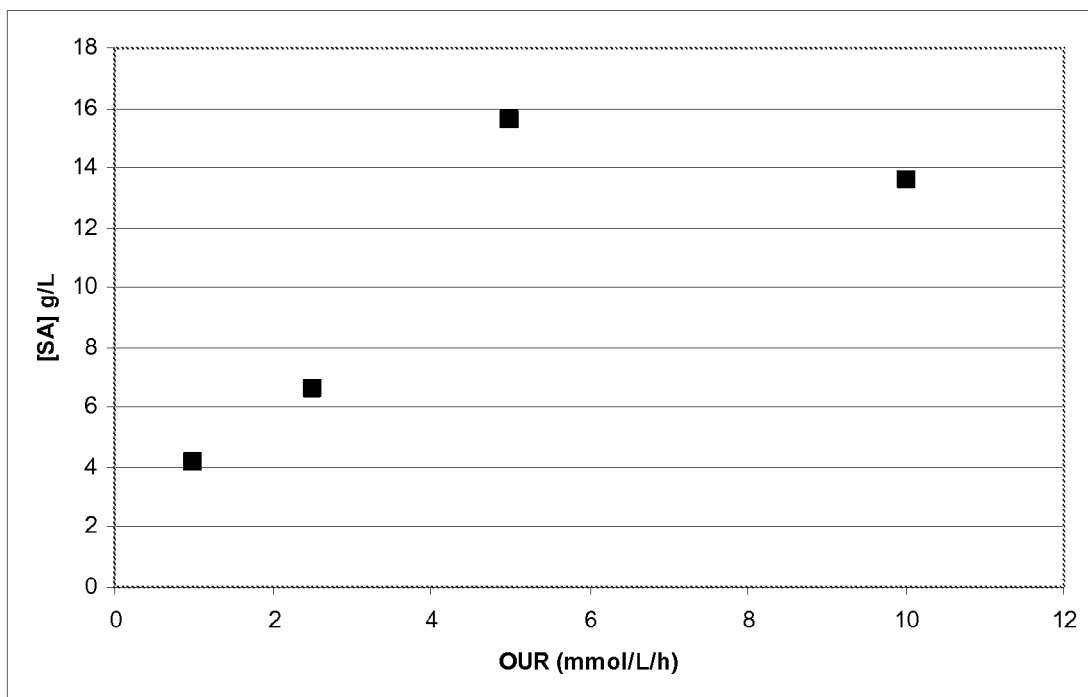

SEQUENCE LISTING

```
<160> NUMBER OF SEQ ID NOS: 10

<210> SEQ ID NO 1
<211> LENGTH: 3148
<212> TYPE: DNA
<213> ORGANISM: Artificial Sequence
<220> FEATURE:
<223> OTHER INFORMATION: Synthetic construct TDH1p-PCKa-TDH1t for
      expression in S. cerevisiae

<400> SEQUENCE: 1
ggatcccttc ccttttacag tgcttcggaa aagcacagcg ttgtccaagg gaacaatttt      60
tcttcaagtt aatgcataag aaatatcttt ttttatgttt agctaagtaa aagcagcttg     120
gagtaaaaaa aaaaatgagt aaatttctcg atggattagt ttctcacagg taacataaca     180
aaaaccaaga aaagcccgct tctgaaaact acagttgact tgtatgctaa agggccagac     240
taatgggagg agaaaaagaa acgaatgtat atgctcattt acactctata tcaccatatg     300
gaggataagt tgggctgagc ttctgatcca atttattcta tccattagtt gctgatatgt     360
cccaccagcc aacacttgat agtatctact cgccattcac ttccagcagc gccagtaggg     420
ttgttgagct tagtaaaaat gtgcgcacca caagcctaca tgactccacg tcacatgaaa     480
ccacaccgtg gggccttgtt gcgctaggaa taggatatgc gacgaagacg cttctgctta     540
gtaaccacac cacattttca gggggtcgat ctgcttgctt cctttactgt cacgagcggc     600
ccataatcgc gctttttttt taaaaggcgc gagacagcaa acaggaagct cgggtttcaa     660
ccttcggagt ggtcgcagat ctggagactg gatctttaca atacagtaag gcaagccacc     720
atctgcttct taggtgcatg cgacggtatc cacgtgcaga acaacatagt ctgaagaagg     780
gggggaggag catgttcatt ctctgtagca gtaagagctt ggtgataatg accaaaactg     840
```

```
gagtctcgaa atcatataaa tagacaatat attttcacac aatgagattt gtagtacagt      900
tctattctct ctcttgcata aataagaaat tcatcaagaa cttggtttga tatttcacca      960
acacacacaa aaaacagtac ttcactaaat ttacacacaa acaaaatga ccgatttgaa      1020
ccaattgact caagaattgg gtgctttggg tattcacgat gtccaagaag ttgtctacaa     1080
cccatcttac gaattgttgt ttgctgaaga aaccaagcca ggtttggaag gttacgaaaa     1140
gggtactgtt accaaccaag gtgctgttgc tgtcaacacc ggtatcttca ccggtcgttc     1200
tccaaaggac aaatacattg tcttggatga caagaccaag gacactgtct ggtggacttc     1260
tgaaaaggtc aagaacgaca acaaaccaat gtcccaagac acttggaact ctttaaaggg     1320
tttagtcgct gaccaattgt ctggtaagag attattcgtt gtcgatgctt tctgtggtgc     1380
caacaaggac accagattag ctgtcagagt tgtcactgaa gttgcttggc aagctcactt     1440
cgttaccaac atgttcatca gaccatctgc tgaagaattg aaaggtttca gccagatttt     1500
cgttgtcatg aacggtgcca aatgtaccaa cccaaactgg aaggaacaag gtttgaactc     1560
tgaaaacttt gttgctttca acatcactga aggtgttcaa ttgattggtg gtacctggta     1620
cggtggtgaa atgaagaagg gtatgttctc catgatgaac tacttcttgc cattgagagg     1680
tattgcttcc atgcactgtt ctgccaatgt cggtaaggac ggtgacactg ccatcttctt     1740
cggtctatcc ggtaccggta agaccacttt gtccactgac ccaaagagac aattgattgg     1800
tgatgacgaa cacggttggg atgacgaagg tgttttcaac tttgaaggtg gttgttacgc     1860
caagaccatc aacttatctg ctgaaaatga accagatatc tacggtgcca tcaagcgtga     1920
cgctctattg gaaaacgttg ttgttttgga caatggtgac gtcgattatg ctgacggttc     1980
caagactgaa acaccagag tttcttaccc aatctaccat attcaaaaca ttgtcaagcc     2040
agtttccaag gctggtccag ctaccaaagt tatcttcttg tctgctgatg ctttcggtgt     2100
tttgcctcct gtttccaagt tgactccaga acaaaccaag tactacttct tgtctggttt     2160
caccgccaag ttggctggta ctgaaagagg tatcactgaa ccaactccaa ctttctctgc     2220
ttgtttcggt gctgcctttt tgtctttgca cccaactcaa tacgctgaag ttttggtcaa     2280
gagaatgcaa gaatctggtg ctgaagctta cttggtcaac actggttgga acggtaccgg     2340
taagagaatc tccatcaaag ataccagagg tatcatcgat gccatcttgg atggttccat     2400
tgacaaggct gaaatgggtt cttttgccaat tttcgatttc tccattccaa aggctttgcc     2460
aggtgtcaac ccagccatct tagacccaag agacacctac gctgacaaag ctcaatggga     2520
agaaaaggct caagacttgg ctggtagatt cgtcaagaac ttcgaaaaat acactggtac     2580
tgctgaaggt caagctttgg ttgctgctgg tccaaaggcc taaggcccgg gcataaagca     2640
atcttgatga ggataatgat tttttttga atatacataa atactaccgt ttttctgcta     2700
gatttgtga agacgtaaat aagtacatat tactttttaa gccaagacaa gattaagcat     2760
taactttacc cttttctctt ctaagtttca atactagtta tcactgttta aaagttatgg     2820
cgagaacgtc ggcggttaaa atatattacc ctgaacgtgg tgaattgaag ttctaggatg     2880
gtttaaagat ttttcctttt tgggaaataa gtaaacaata tattgctgcc tttgcaaaac     2940
gcacataccc acaatatgtg actattggca aagaacgcat tatcctttga agaggtggat     3000
actgatacta agagagtctc tattccggct ccacttttag tccagagatt acttgtcttc     3060
ttacgtatca gaacaagaaa gcatttccaa agtaattgca tttgcccttg agcagtatat     3120
atatactaag aaggcgcgcc gcggccgc                                        3148
```

<210> SEQ ID NO 2
<211> LENGTH: 4959
<212> TYPE: DNA
<213> ORGANISM: Artificial Sequence
<220> FEATURE:
<223> OTHER INFORMATION: Synthetic construct TDH3p-FRDg-TDH3t for expression in S. cerevisiae

<400> SEQUENCE: 2

```
ggatccggcg cgccctattt tcgaggacct tgtcaccttg agcccaagag agccaagatt     60
taaattttcc tatgacttga tgcaaattcc caaagctaat aacatgcaag acacgtacgg    120
tcaagaagac atatttgacc tcttaacagg ttcagacgcg actgcctcat cagtaagacc    180
cgttgaaaag aacttacctg aaaaaaacga atatatacta gcgttgaatg ttagcgtcaa    240
caacaagaag tttaatgacg cggaggccaa ggcaaaaaga ttccttgatt acgtaaggga    300
gttagaatca ttttgaataa aaaacacgct ttttcagttc gagtttatca ttatcaatac    360
tgccatttca aagaatacgt aaataattaa tagtagtgat tttcctaact ttatttagtc    420
aaaaaattag cctttttaatt ctgctgtaac ccgtacatgc ccaaaatagg gggcgggtta    480
cacagaatat ataacatcgt aggtgtctgg gtgaacagtt tattcctggc atccactaaa    540
tataatggag cccgcttttt aagctggcat ccagaaaaaa aagaatccc agcaccaaaa    600
tattgttttc ttcaccaacc atcagttcat aggtccattc tcttagcgca actacagaga    660
acagggggcac aaacaggcaa aaaacgggca caacctcaat ggagtgatgc aacctgcctg    720
gagtaaatga tgacacaagg caattgaccc acgcatgtat ctatctcatt ttcttacacc    780
ttctattacc ttctgctctc tctgatttgg aaaaagctga aaaaaaaggt tgaaaccagt    840
tccctgaaat tattccccta cttgactaat aagtatataa agacggtagg tattgattgt    900
aattctgtaa atctatttct taaacttctt aaattctact tttatagtta gtctttttttt    960
tagtttttaaa acaccaagaa cttagtttcg aataaacaca cataaacaaa caaaatggtt   1020
gatggtagat cttctgcttc cattgttgcc gttgacccag aaagagctgc cagagaaaga   1080
gatgctgctg ccagagcttt gttgcaagac tctccattgc acaccaccat gcaatacgct   1140
acctctggtt tggaattgac tgttccatac gctttgaagg ttgttgcttc tgctgacact   1200
ttcgacagag ccaaggaagt tgctgatgaa gtcttgagat gtgcctggca attggctgac   1260
accgttttga actcttcaa cccaaactct gaagtctctt tagtcggtag attaccagtc   1320
ggtcaaaagc atcaaatgtc tgctccattg aaacgtgtca tggcttgttg tcaaagagtc   1380
tacaactcct ctgctggttg tttcgaccca tccactgctc cagttgccaa ggctttgaga   1440
gaaattgctt tgggtaagga agaaacaat gcttgtttgg aagctttgac tcaagcttgt   1500
accttgccaa actctttcgt cattgatttc gaagctggta ctatctccag aaagcacgaa   1560
cacgcttctt tggatttggg tggtgtttcc aagggttaca tcgtcgatta cgtcattgac   1620
aacatcaatg ctgctggttt ccaaaacgtt tcctttgact ggggtggtga ctgtcgtgcc   1680
tccggtatga acgccagaaa cactccatgg gttgtcggta tcactagacc tccttccttg   1740
gacatgttgc aaaccctcc aaaggaagct tcttacatct ccgtcatctc tttggacaat   1800
gaagctttgg ctacctctgg tgattacgaa aacttgatct acactgctga cgataaacca   1860
ttgacctgta cctacgattg gaaggtaag gaattgatga agccatctca atccaatatc   1920
gctcaagttt ccgtcaagtg ttactctgcc atgtacgctg acgctttggc taccgcttgt   1980
ttcatcaagc gtgacccagc caaggtcaga caattgttgg atggttggag atacgttaga   2040
```

```
gacaccgtca gagattaccg tgtctacgtc agagaaaacg aaagagttgc caagatgttc    2100
gaaattgcca ctgaagatgc tgaaatgaga aagagaagaa tttccaacac tttaccagct    2160
cgtgtcattg ttgttggtgg tggtttggct ggtttgtccg ctgccattga agctgctggt    2220
tgtggtgctc aagttgtttt gatggaaaag gaagccaagt tgggtggtaa ctctgccaag    2280
gctacctctg gtatcaacgg ttggggtact agagctcaag ctaaggcttc cattgtcgat    2340
ggtggtaagt acttcgaaag agatacctac aagtctggta tcggtggtaa caccgatcca    2400
gctttggtta agactttgtc catgaaatct gctgacgcta tcggttggtt gacttctcta    2460
ggtgttccat tgactgtttt gtcccaatta ggtggtcact ccagaaagag aactcacaga    2520
gctccagaca agaaggatgg tactccattg ccaattggtt tcaccatcat gaaaacttta    2580
gaagatcatg ttagaggtaa cttgtccggt agaatcacca tcatggaaaa ctgttccgtt    2640
acctctttgt tgtctgaaac caaggaaaga ccagacggta ccaagcaaat cagagttacc    2700
ggtgtcgaat tcactcaagc tggttctggt aagaccacca ttttggctga tgctgttatc    2760
ttggccaccg gtggtttctc caacgacaag actgctgatt ctttgttgag agaacatgcc    2820
ccacacttgg ttaacttccc aaccaccaac ggtccatggg ctactggtga tggtgtcaag    2880
ttggctcaaa gattaggtgc tcaattggtc gatatgacca ggttcaatt gcacccaact    2940
ggtttgatca acccaaagga cccagccaac ccaaccaaat tcttgggtcc agaagctcta    3000
agaggttctg tggtgttttt gttgaacaaa caaggtaaga gatttgtcaa cgaattggat    3060
ttgagatctg ttgtttccaa ggccatcatg aacaaggtg ctgaatacc aggttctggt    3120
ggttccatgt ttgcttactg tgtcttgaac gctgctgctc aaaaattgtt tggtgtttcc    3180
tctcacgaat tctactggaa gaagatgggt ttgttcgtca aggctgacac catgagagac    3240
ttggctgctt tgattggttg tccagttgaa tccgttcaac aaactttaga agaatacgaa    3300
agattatcca tctctcaaag atcttgtcca attaccagaa aatctgttta cccatgtgtt    3360
ttgggtacca aagtccata ctatgtcgcc tttgtcactc catctatcca ctacaccatg    3420
ggtggttgtt tgatttctcc atctgctgaa atccaaatga gaacacttc ttccagagct    3480
ccattgtccc actccaaccc aatcttgggt ttattcggtg ctggtgaagt caccggtggt    3540
gtccacggtg gtaacagatt aggtggtaac tctttgttgg aatgtgttgt tttcggtaga    3600
attgccggtg acagagcttc taccattttg caaagaaagt cctctgcttt gtctttcaag    3660
gtctggacca ctgttgtttt gagagaagtc agagaaggtg gtgtctacgg tgctggttcc    3720
cgtgtcttga gattcaactt accaggtgct ctacaaagat ctggtctatc cttgggtcaa    3780
ttcattgcca tcagaggtga ctgggacggt caacaattga ttggttacta ctctccaatc    3840
actttgccag acgatttggg tatgattgac attttggcca gatctgacaa gggtactttta    3900
cgtgaatgga tctctgcttt ggaaccaggt gacgctgtcg aaatgaaggc ttgtggtggt    3960
ttggtcatcg aaagaagatt atctgacaag cacttcgttt tcatgggtca cattatcaac    4020
aagctatgtt tgattgctgg tggtaccggt gttgctccaa tgttgcaaat catcaaggcc    4080
gctttcatga agccattcat cgacactttg gaatccgtcc acttgatcta cgctgctgaa    4140
gatgtcactg aattgactta cagagaagtt ttggaagaac gtcgtcgtga atccagaggt    4200
aaattcaaga aaactttcgt tttgaacaga cctcctccat tatggactga cggtgtcggt    4260
ttcatcgacc gtggtatctt gaccaaccac gttcaaccac catctgacaa cttattggtt    4320
gccatctgtg gtccaccagt tatgcaaaga attgtcaagg ccactttaaa gactttaggt    4380
tacaacatga acttggtcag aaccgttgac gaaactgaac catctggaag ttaaggcccg    4440
```

-continued

```
ggcgtgaatt tactttaaat cttgcattta aataaatttt ctttttatag ctttatgact      4500
tagtttcaat ttatatacta ttttaatgac attttcgatt cattgattga aagctttgtg      4560
ttttttcttg atgcgctatt gcattgttct tgtcttttc gccacatgta atatctgtag       4620
tagatacctg atacattgtg gatgctgagt gaaattttag ttaataatgg aggcgctctt      4680
aataattttg gggatattgg cttttttttt taaagtttac aaatgaattt tttccgccag      4740
gataacgatt ctgaagttac tcttagcgtt cctatcggta cagccatcaa atcatgccta      4800
taaatcatgc ctatatttgc gtgcagtcag tatcatctac atgaaaaaaa ctcccgcaat      4860
ttcttataga atacgttgaa aattaaatgt acgcgccaag ataagataac atatatctag      4920
atgcagtaat atacacagat tccggccggc cgcggccgc                             4959
```

<210> SEQ ID NO 3
<211> LENGTH: 2950
<212> TYPE: DNA
<213> ORGANISM: Artificial Sequence
<220> FEATURE:
<223> OTHER INFORMATION: Synthetic construct TDH1p-FUMR-TDH1t for
    expression in S. cerevisiae

<400> SEQUENCE: 3

```
ggatcccttc cctttacag tgcttcggaa aagcacagcg ttgtccaagg gaacaatttt       60
tcttcaagtt aatgcataag aaatatcttt ttttatgttt agctaagtaa aagcagcttg      120
gagtaaaaaa aaaaatgagt aaatttctcg atggattagt ttctcacagg taacataaca     180
aaaaccaaga aaagcccgct tctgaaaact acagttgact tgtatgctaa agggccagac     240
taatgggagg agaaaagaa acgaatgtat atgctcattt acactctata tcaccatatg      300
gaggataagt tgggctgagc ttctgatcca atttattcta tccattagtt gctgatatgt     360
cccaccagcc aacacttgat agtatctact cgccattcac ttccagcagc gccagtaggg     420
ttgttgagct tagtaaaaat gtgcgcacca caagcctaca tgactccacg tcacatgaaa    480
ccacaccgtg gggccttgtt gcgctaggaa taggatatgc gacgaagacg cttctgctta    540
gtaaccacac acattttca gggggtcgat ctgcttgctt cctttactgt cacgagcggc     600
ccataatcgc gctttttttt taaaaggcgc gagacagcaa acaggaagct cgggtttcaa     660
ccttcggagt ggtcgcagat ctggagactg gatctttaca atacagtaag gcaagccacc     720
atctgcttct taggtgcatg cgacggtatc cacgtgcaga acaacatagt ctgaagaagg     780
gggggaggag catgttcatt ctctgtagca gtaagagctt ggtgataatg accaaaactg    840
gagtctcgaa atcatataaa tagacaatat attttcacac aatgagattt gtagtacagt    900
tctattctct ctcttgcata aataagaaat tcatcaagaa cttggtttga tatttcacca     960
acacacacaa aaacagtac ttcactaaat ttacacacaa acaaaatgt cctctgcttc       1020 tgctgctttg caaaaattca gagctgaaag agatacctcc ggtgacttgc aagttccagc    1080
tgaccgttac tggggtgctc aaactcaaag atctttgcaa aactttgaca ttggtggtcc    1140
aactgaaaga atgccagaac cattaatcag agctttcggt gttttgaaga aggctgctgc    1200
caccgtcaac atgacctacg gtttgggacc aaaggttggt gaagccatcc aaaggctgc    1260 tgacgaagtt atcgatggtt ctttgattga ccatttccca ttggttgtct ggcaaaccgg    1320
ttctggtact caaaccaaga tgaacgtcaa tgaagtcatc tccaacagag ccattgaatt    1380
gttgggtggt gaattaggtt ccaaggctcc agtccaccca aacgatcatg tcaacatgtc    1440
tcaatcttcc aacgacactt tcccaactgc catgcacgtt gctgccgttg ttgaaattca    1500
```

```
cggtagattg attccagctt tgaccacttt gagagatgct ttgcaagcca aatctgctga    1560
attcgaacac atcatcaaga ttggtagaac ccacttgcaa gatgctaccc cattgacttt    1620
aggtcaagaa ttctccggtt acactcaaca attgacctac ggtattgctc gtgttcaagg    1680
tactttggaa agattataca acttggctca aggtggtact gctgtcggta ctggtttgaa    1740
caccagaaag ggtttcgatg ccaaggttgc tgaagccatt gcttccatca ctggtttacc    1800
attcaagacc gctccaaaca aattcgaagc tttggctgct cacgcgctt tggttgaagc     1860 tcacggtgct ttgaacaccg ttgcttgttc tttgatgaag attgccaacg atatccgtta    1920
cttgggttct ggtccaagat gtggtttagg tgaattgtct ctaccagaaa acgaaccagg    1980
ttcttccatc atgccaggta aggtcaaccc aactcaatgt gaagctatga ccatggtttg    2040
tgctcaagtc atgggtaaca acactgccat ctctgttgct ggttccaacg gtcaattcga    2100
attgaatgtc tttaaaccag tcatgatcaa gaacttgatc caatccatca gattaatctc    2160
tgacgcttcc atctctttca ccaagaactg tgttgtcggt attgaagcta acgaaaagaa    2220
gatctcctcc atcatgaacg aatctttgat gttggtcact gctttgaacc ctcacattgg    2280
ttacgacaag gctgccaagt gtgccaagaa ggctcacaag gaaggtacca ctttgaaaga    2340
agctgctcta tctttgggtt acttgacctc tgaagaattc gaccaatggg ttagacctga    2400
ggacatgatt tctgccaagg attaaggccc gggcataaag caatcttgat gaggataatg    2460
attttttttt gaatatacat aaatactacc gttttctgc tagattttgt gaagacgtaa      2520
ataagtacat attacttttt aagccaagac aagattaagc attaacttta ccctttctc      2580 ttctaagttt caatactagt tatcactgtt taaaagttat ggcgagaacg tcggcggtta    2640
aaatatatta ccctgaacgt ggtgaattga agttctagga tggtttaaag attttttcctt    2700 tttgggaaat aagtaaacaa tatattgctg cctttgcaaa acgcacatac ccacaatatg    2760
tgactattgg caaagaacgc attatccttt gaagaggtgg atactgatac taagagagtc    2820
tctattccgg ctccactttt agtccagaga ttacttgtct tcttacgtat cagaacaaga    2880
aagcatttcc aaagtaattg catttgccct tgagcagtat atatatacta agaaggcgcg    2940
ccgcggccgc                                                           2950
```

<210> SEQ ID NO 4
<211> LENGTH: 1966
<212> TYPE: DNA
<213> ORGANISM: Artificial Sequence
<220> FEATURE:
<223> OTHER INFORMATION: Synthetic construct TDH3p-MDH3-TDH3t for
      expression in S. cerevisiae

<400> SEQUENCE: 4

```
ggatccggcg cgccacgcgt ggccggcctt agtcaaaaaa ttagcctttt aattctgctg      60
taacccgtac atgcccaaaa tagggggcgg gttacacaga atatataaca tcgtaggtgt     120
ctgggtgaac agtttattcc tggcatccac taaatataat ggagcccgct ttttaagctg     180
gcatccagaa aaaaaagaa tcccagcacc aaaatattgt tttcttcacc aaccatcagt      240
tcataggtcc attctcttag cgcaactaca gagaacaggg gcacaaacag caaaaaacg      300 ggcacaacct caatggagtg atgcaacctg cctggagtaa atgatgacac aaggcaattg     360
acccacgcat gtatctatct cattttctta caccttctat taccttctgc tctctctgat     420
ttggaaaaag ctgaaaaaaa aggttgaaac cagttccctg aaattattcc cctacttgac     480
taataagtat ataagacgg taggtattga ttgtaattct gtaaatctat tcttaaaact     540
```

```
tcttaaattc tactttata gttagtcttt ttttagttt taaaacacca agaacttagt      600
ttcgaataaa cacacataaa caaacaaaat ggttaaggtt gccatcttag gtgcttctgg     660
tggtgtcggt caaccattat ctctattatt gaaattgtct ccatacgttt ctgaattggc     720
tttgtacgat atcagagctg ctgaaggtat tggtaaggat tgtcccaca tcaacaccaa      780 ctcctcttgt gttggttacg acaaggattc catcgaaaac actttgtcca atgctcaagt     840
tgtcttgatt ccagctggtg ttccaagaaa gccaggtttg accagagatg atttgttcaa     900
gatgaacgct ggtatcgtta agtctttggt tactgctgtc ggtaaatttg ccccaaacgc     960
tcgtatctta gtcatctcca accctgttaa ctctttggtt ccaattgccg ttgaaacttt    1020
gaagaagatg ggtaagttca agccaggtaa cgttatgggt gtcaccaact ggatttggt     1080 cagagctgaa actttcttgg ttgactactt gatgttgaag aacccaaaga tcggtcaaga    1140
acaagacaag accaccatgc acagaaaggt caccgtcatc ggtggtcact ctggtgaaac    1200
catcattcca atcatcactg acaaatcctt ggtttttccaa ttggacaagc aatacgaaca    1260
tttcatccac agagtccaat cggtggtga cgaaattgtc aaggccaagc aaggtgccgg     1320
ttctgctacc ttgtccatgg ctttcgctgg tgccaaattt gctgaagaag tcttacgttc    1380
tttccacaac gaaaagccag aaactgaatc tttgtctgct ttcgtctact gccaggtttt    1440
gaagaacggt aagaaggctc aacaattagt cggtgacaac tccattgaat acttctcttt    1500
gccaattgtt ttgagaaacg gttccgttgt ttccattgac acttctgttt tggaaaaatt    1560
gtctccaaga gaagaacaat tggtcaacac tgctgtcaag gaattgagaa agaacattga    1620
aaagggtaag tctttcatct tggacagtta aggtgaattt actttaaatc ttgcatttaa    1680
ataaattttc ttttttatagc tttatgactt agtttcaatt tatatactat tttaatgaca    1740
ttttcgattc attgattgaa agctttgtgt ttttcttga tgcgctattg cattgttctt    1800
gtctttttcg ccacatgtaa tatctgtagt agatacctga tacattgtgg atgctgagtg    1860
aaattttagt taataatgga ggcgctctta ataattttgg ggatattggc ttttttttt     1920 aaagtttaca aatgaatttt ttccgccagg atgggcccgc ggccgc                    1966
```

<210> SEQ ID NO 5
<211> LENGTH: 2240
<212> TYPE: DNA
<213> ORGANISM: Artificial Sequence
<220> FEATURE:
<223> OTHER INFORMATION: Synthetic construct Eno1p-SpMAE1-ENOt for expression in S. cerevisiae

<400> SEQUENCE: 5

```
ggatccggcg cgccccgcgg aaccgccaga tattcattac ttgacgcaaa agcgtttgaa      60
ataatgacga aaagaaggaa agaaaaaaaa agaaaaatac cgcttctagg cgggttatct     120
actgatccga gcttccacta ggatagcacc caaacacctg catatttgga cgacctttac     180
ttacaccacc aaaaaccact ttcgcctctc ccgcccctga taacgtccac taattgagcg    240
attacctgag cggtcctctt ttgtttgcag catgagactt gcatactgca atcgtaagt     300 agcaacgtct caaggtcaaa actgtatgga accttgtca cctcacttaa ttctagctag     360
cctaccctgc aagtcaagag gtctccgtga ttcctagcca cctcaaggta tgcctctccc    420
cggaaactgt ggcctttct ggcacacatg atctccacga tttcaacata taaatagctt     480
ttgataatgg caatattaat caaatttatt ttacttcttt cttgtaacat ctctcttgta     540 atccccttatt ccttctagct attttttcata aaaaaccaag caactgctta tcaacacaca    600
```

```
aacactaaaa caaaatgggt gaattgaagg aaatcttgaa gcaacgttac catgaattgt    660
tggactggaa cgtcaaggct ccacacgttc cattgtctca agattgaag catttcacct    720
ggtcctggtt tgcttgtacc atggccactg gtggtgtcgg tttgatcatt ggttctttcc    780
cattcagatt ctacggtttg aacaccattg gtaagattgt ctacatctta caaatcttct    840
tattctcttt gtttggttct tgtatgttgt tcagattcat caaatacccca tctaccatca    900
aggactcctg gaaccaccac ttggaaaaat tattcattgc tacctgtttg ctatccatct    960
ccactttcat tgacatgttg gccatctacg cttacccaga cactggtgaa tggatggtct   1020
gggttatcag aatcttatac tacatctacg ttgctgtctc tttcatctac tgtgtcatgg   1080
ctttcttcac catttttcaac aaccacgttt acaccattga aactgcttct ccagcttgga   1140
tcttaccaat tttcccacca atgatctgtg gtgtcattgc tggtgctgtc aactccactc   1200
aaccagctca ccaattgaag aacatggtta tcttcggtat cttattccaa ggtttgggtt   1260
tctgggttta cttgttgttg tttgctgtca acgttttgag attcttcacc gttggtttgg   1320
ccaagcctca agacagacca ggtatgttca tgtttgttgg tccaccagct ttctccggtt   1380
tggctttgat caacattgcc cgtggtgcta tgggttccag accatacatt ttcgtcggtg   1440
ccaattcttc tgaatacttg ggtttcgttt ccactttcat ggccattttc atctggggtt   1500
tggctgcttg gtgttactgt ttggccatgg tttctttctt ggctggtttc ttcaccagag   1560
ctccattgaa atttgcttgt ggttggtttg ctttcatctt cccaaacgtc ggtttcgtta   1620
actgtaccat tgaaattggt aagatgattg actccaaggc cttccaaatg ttcggtcaca   1680
tcatcggtgt catcctatgt atccaatgga tcttgttgat gtacttgatg gtcagagctt   1740
tcttggtcaa cgatttgtgt tacccaggta aggatgaaga tgctcaccca cctccaaagc   1800
caaacactgg tgttttgaac ccaactttcc caccagaaaa ggctccagct tctttggaaa   1860
aggttgacac ccacgttact tccactggtg gtgaatctga tcctccatct tctgaacacg   1920
aaagcgttta agagcttttg attaagcctt ctagtccaaa aaacacgttt ttttgtcatt   1980
tatttcattt tcttagaata gtttagttta ttcatttttat agtcacgaat gttttatgat   2040
tctatatagg gttgcaaaca agcatttttc attttatgtt aaaacaattt caggtttacc   2100
ttttattctg cttgtggtga cgcgggtatc cgcccgctct tttggtcacc catgtatttta   2160
attgcataaa taattcttaa aagtggagct agtctatttc tatttacata cctctcattt   2220
ctcatttcct ccgcggccgc                                              2240
```

<210> SEQ ID NO 6
<211> LENGTH: 538
<212> TYPE: PRT
<213> ORGANISM: Artificial Sequence
<220> FEATURE:
<223> OTHER INFORMATION: Actinobacillus succinogenes phosphoenolpyruvate carboxykinase amino acid sequence, with EGY to DAF modification at pos 120 - 122.

<400> SEQUENCE: 6

```
Met Thr Asp Leu Asn Lys Leu Val Lys Glu Leu Asn Asp Leu Gly Leu
1               5                   10                  15

Thr Asp Val Lys Glu Ile Val Tyr Asn Pro Ser Tyr Glu Gln Leu Phe
            20                  25                  30

Glu Glu Glu Thr Lys Pro Gly Leu Glu Gly Phe Asp Lys Gly Thr Leu
        35                  40                  45

Thr Thr Leu Gly Ala Val Ala Val Asp Thr Gly Ile Phe Thr Gly Arg
```

```
            50                  55                  60
Ser Pro Lys Asp Lys Tyr Ile Val Cys Asp Glu Thr Thr Lys Asp Thr
 65                  70                  75                  80

Val Trp Trp Asn Ser Glu Ala Ala Lys Asn Asp Asn Lys Pro Met Thr
                 85                  90                  95

Gln Glu Thr Trp Lys Ser Leu Arg Glu Leu Val Ala Lys Gln Leu Ser
                100                 105                 110

Gly Lys Arg Leu Phe Val Val Asp Ala Phe Cys Gly Ala Ser Glu Lys
                115                 120                 125

His Arg Ile Gly Val Arg Met Val Thr Glu Val Ala Trp Gln Ala His
                130                 135                 140

Phe Val Lys Asn Met Phe Ile Arg Pro Thr Asp Glu Glu Leu Lys Asn
145                 150                 155                 160

Phe Lys Ala Asp Phe Thr Val Leu Asn Gly Ala Lys Cys Thr Asn Pro
                165                 170                 175

Asn Trp Lys Glu Gln Gly Leu Asn Ser Glu Asn Phe Val Ala Phe Asn
                180                 185                 190

Ile Thr Glu Gly Ile Gln Leu Ile Gly Gly Thr Trp Tyr Gly Gly Glu
                195                 200                 205

Met Lys Lys Gly Met Phe Ser Met Met Asn Tyr Phe Leu Pro Leu Lys
                210                 215                 220

Gly Val Ala Ser Met His Cys Ser Ala Asn Val Gly Lys Asp Gly Asp
225                 230                 235                 240

Val Ala Ile Phe Phe Gly Leu Ser Gly Thr Gly Lys Thr Thr Leu Ser
                245                 250                 255

Thr Asp Pro Lys Arg Gln Leu Ile Gly Asp Asp Glu His Gly Trp Asp
                260                 265                 270

Glu Ser Gly Val Phe Asn Phe Glu Gly Gly Cys Tyr Ala Lys Thr Ile
                275                 280                 285

Asn Leu Ser Gln Glu Asn Glu Pro Asp Ile Tyr Gly Ala Ile Arg Arg
                290                 295                 300

Asp Ala Leu Leu Glu Asn Val Val Arg Ala Asp Gly Ser Val Asp
305                 310                 315                 320

Phe Asp Asp Gly Ser Lys Thr Glu Asn Thr Arg Val Ser Tyr Pro Ile
                325                 330                 335

Tyr His Ile Asp Asn Ile Val Arg Pro Val Ser Lys Ala Gly His Ala
                340                 345                 350

Thr Lys Val Ile Phe Leu Thr Ala Asp Ala Phe Gly Val Leu Pro Pro
                355                 360                 365

Val Ser Lys Leu Thr Pro Glu Gln Thr Glu Tyr Tyr Phe Leu Ser Gly
                370                 375                 380

Phe Thr Ala Lys Leu Ala Gly Thr Glu Arg Gly Val Thr Glu Pro Thr
385                 390                 395                 400

Pro Thr Phe Ser Ala Cys Phe Gly Ala Ala Phe Leu Ser Leu His Pro
                405                 410                 415

Ile Gln Tyr Ala Asp Val Leu Val Glu Arg Met Lys Ala Ser Gly Ala
                420                 425                 430

Glu Ala Tyr Leu Val Asn Thr Gly Trp Asn Gly Thr Gly Lys Arg Ile
                435                 440                 445

Ser Ile Lys Asp Thr Arg Gly Ile Ile Asp Ala Ile Leu Asp Gly Ser
                450                 455                 460

Ile Glu Lys Ala Glu Met Gly Glu Leu Pro Ile Phe Asn Leu Ala Ile
465                 470                 475                 480
```

```
Pro Lys Ala Leu Pro Gly Val Asp Pro Ala Ile Leu Asp Pro Arg Asp
            485                 490                 495

Thr Tyr Ala Asp Lys Ala Gln Trp Gln Val Lys Ala Glu Asp Leu Ala
            500                 505                 510

Asn Arg Phe Val Lys Asn Phe Val Lys Tyr Thr Ala Asn Pro Glu Ala
            515                 520                 525

Ala Lys Leu Val Gly Ala Gly Pro Lys Ala
            530                 535

<210> SEQ ID NO 7
<211> LENGTH: 1139
<212> TYPE: PRT
<213> ORGANISM: Artificial Sequence
<220> FEATURE:
<223> OTHER INFORMATION: Glycosomal Trypanosoma brucei fumarate
      reductase (FRDg) amino acid sequence lacking 3 aa C-terminal
      targeting signal.

<400> SEQUENCE: 7

Met Val Asp Gly Arg Ser Ser Ala Ser Ile Val Ala Val Asp Pro Glu
1               5                   10                  15

Arg Ala Ala Arg Glu Arg Asp Ala Ala Ala Arg Ala Leu Leu Gln Asp
            20                  25                  30

Ser Pro Leu His Thr Thr Met Gln Tyr Ala Thr Ser Gly Leu Glu Leu
        35                  40                  45

Thr Val Pro Tyr Ala Leu Lys Val Val Ala Ser Ala Asp Thr Phe Asp
    50                  55                  60

Arg Ala Lys Glu Val Ala Asp Glu Val Leu Arg Cys Ala Trp Gln Leu
65                  70                  75                  80

Ala Asp Thr Val Leu Asn Ser Phe Asn Pro Asn Ser Glu Val Ser Leu
                85                  90                  95

Val Gly Arg Leu Pro Val Gly Gln Lys His Gln Met Ser Ala Pro Leu
            100                 105                 110

Lys Arg Val Met Ala Cys Cys Gln Arg Val Tyr Asn Ser Ser Ala Gly
        115                 120                 125

Cys Phe Asp Pro Ser Thr Ala Pro Val Ala Lys Ala Leu Arg Glu Ile
    130                 135                 140

Ala Leu Gly Lys Glu Arg Asn Asn Ala Cys Leu Glu Ala Leu Thr Gln
145                 150                 155                 160

Ala Cys Thr Leu Pro Asn Ser Phe Val Ile Asp Phe Glu Ala Gly Thr
                165                 170                 175

Ile Ser Arg Lys His Glu His Ala Ser Leu Asp Leu Gly Gly Val Ser
            180                 185                 190

Lys Gly Tyr Ile Val Asp Tyr Val Ile Asp Asn Ile Asn Ala Ala Gly
        195                 200                 205

Phe Gln Asn Val Phe Phe Asp Trp Gly Gly Asp Cys Arg Ala Ser Gly
    210                 215                 220

Met Asn Ala Arg Asn Thr Pro Trp Val Val Gly Ile Thr Arg Pro Pro
225                 230                 235                 240

Ser Leu Asp Met Leu Pro Asn Pro Lys Glu Ala Ser Tyr Ile Ser
                245                 250                 255

Val Ile Ser Leu Asp Asn Glu Ala Leu Ala Thr Ser Gly Asp Tyr Glu
            260                 265                 270

Asn Leu Ile Tyr Thr Ala Asp Asp Lys Pro Leu Thr Cys Thr Tyr Asp
        275                 280                 285
```

-continued

```
Trp Lys Gly Lys Glu Leu Met Lys Pro Ser Gln Ser Asn Ile Ala Gln
    290                 295                 300
Val Ser Val Lys Cys Tyr Ser Ala Met Tyr Ala Asp Ala Leu Ala Thr
305                 310                 315                 320
Ala Cys Phe Ile Lys Arg Asp Pro Ala Lys Val Arg Gln Leu Leu Asp
                325                 330                 335
Gly Trp Arg Tyr Val Arg Asp Thr Val Arg Asp Tyr Arg Val Tyr Val
            340                 345                 350
Arg Glu Asn Glu Arg Val Ala Lys Met Phe Glu Ile Ala Thr Glu Asp
        355                 360                 365
Ala Glu Met Arg Lys Arg Arg Ile Ser Asn Thr Leu Pro Ala Arg Val
    370                 375                 380
Ile Val Val Gly Gly Gly Leu Ala Gly Leu Ser Ala Ala Ile Glu Ala
385                 390                 395                 400
Ala Gly Cys Gly Ala Gln Val Val Leu Met Glu Lys Glu Ala Lys Leu
                405                 410                 415
Gly Gly Asn Ser Ala Lys Ala Thr Ser Gly Ile Asn Gly Trp Gly Thr
            420                 425                 430
Arg Ala Gln Ala Lys Ala Ser Ile Val Asp Gly Gly Lys Tyr Phe Glu
        435                 440                 445
Arg Asp Thr Tyr Lys Ser Gly Ile Gly Gly Asn Thr Asp Pro Ala Leu
    450                 455                 460
Val Lys Thr Leu Ser Met Lys Ser Ala Asp Ala Ile Gly Trp Leu Thr
465                 470                 475                 480
Ser Leu Gly Val Pro Leu Thr Val Leu Ser Gln Leu Gly Gly His Ser
                485                 490                 495
Arg Lys Arg Thr His Arg Ala Pro Asp Lys Lys Asp Gly Thr Pro Leu
            500                 505                 510
Pro Ile Gly Phe Thr Ile Met Lys Thr Leu Glu Asp His Val Arg Gly
        515                 520                 525
Asn Leu Ser Gly Arg Ile Thr Ile Met Glu Asn Cys Ser Val Thr Ser
    530                 535                 540
Leu Leu Ser Glu Thr Lys Glu Arg Pro Asp Gly Thr Lys Gln Ile Arg
545                 550                 555                 560
Val Thr Gly Val Glu Phe Thr Gln Ala Gly Ser Gly Lys Thr Thr Ile
                565                 570                 575
Leu Ala Asp Ala Val Ile Leu Ala Thr Gly Gly Phe Ser Asn Asp Lys
            580                 585                 590
Thr Ala Asp Ser Leu Leu Arg Glu His Ala Pro His Leu Val Asn Phe
        595                 600                 605
Pro Thr Thr Asn Gly Pro Trp Ala Thr Gly Asp Gly Val Lys Leu Ala
    610                 615                 620
Gln Arg Leu Gly Ala Gln Leu Val Asp Met Asp Lys Val Gln Leu His
625                 630                 635                 640
Pro Thr Gly Leu Ile Asn Pro Lys Asp Pro Ala Asn Pro Thr Lys Phe
                645                 650                 655
Leu Gly Pro Glu Ala Leu Arg Gly Ser Gly Val Leu Leu Asn Lys
            660                 665                 670
Gln Gly Lys Arg Phe Val Asn Glu Leu Asp Leu Arg Ser Val Val Ser
        675                 680                 685
Lys Ala Ile Met Glu Gln Gly Ala Glu Tyr Pro Gly Ser Gly Gly Ser
    690                 695                 700
Met Phe Ala Tyr Cys Val Leu Asn Ala Ala Ala Gln Lys Leu Phe Gly
```

-continued

```
            705                 710                 715                 720
        Val Ser Ser His Glu Phe Tyr Trp Lys Lys Met Gly Leu Phe Val Lys
                        725                 730                 735

Ala Asp Thr Met Arg Asp Leu Ala Ala Leu Ile Gly Cys Pro Val Glu
                        740                 745                 750

Ser Val Gln Gln Thr Leu Glu Tyr Glu Arg Leu Ser Ile Ser Gln
                        755                 760                 765

Arg Ser Cys Pro Ile Thr Arg Lys Ser Val Tyr Pro Cys Val Leu Gly
                        770                 775                 780

Thr Lys Gly Pro Tyr Tyr Val Ala Phe Val Thr Pro Ser Ile His Tyr
        785                 790                 795                 800

Thr Met Gly Gly Cys Leu Ile Ser Pro Ser Ala Glu Ile Gln Met Lys
                        805                 810                 815

Asn Thr Ser Ser Arg Ala Pro Leu Ser His Ser Asn Pro Ile Leu Gly
                        820                 825                 830

Leu Phe Gly Ala Gly Glu Val Thr Gly Gly Val His Gly Gly Asn Arg
                        835                 840                 845

Leu Gly Gly Asn Ser Leu Leu Glu Cys Val Val Phe Gly Arg Ile Ala
                        850                 855                 860

Gly Asp Arg Ala Ser Thr Ile Leu Gln Arg Lys Ser Ser Ala Leu Ser
        865                 870                 875                 880

Phe Lys Val Trp Thr Thr Val Val Leu Arg Glu Val Arg Glu Gly Gly
                        885                 890                 895

Val Tyr Gly Ala Gly Ser Arg Val Leu Arg Phe Asn Leu Pro Gly Ala
                        900                 905                 910

Leu Gln Arg Ser Gly Leu Ser Leu Gly Gln Phe Ile Ala Ile Arg Gly
                        915                 920                 925

Asp Trp Asp Gly Gln Gln Leu Ile Gly Tyr Tyr Ser Pro Ile Thr Leu
                        930                 935                 940

Pro Asp Asp Leu Gly Met Ile Asp Ile Leu Ala Arg Ser Asp Lys Gly
        945                 950                 955                 960

Thr Leu Arg Glu Trp Ile Ser Ala Leu Glu Pro Gly Asp Ala Val Glu
                        965                 970                 975

Met Lys Ala Cys Gly Gly Leu Val Ile Glu Arg Arg Leu Ser Asp Lys
                        980                 985                 990

His Phe Val Phe Met Gly His Ile  Ile Asn Lys Leu Cys  Leu Ile Ala
                        995                 1000                1005

Gly Gly  Thr Gly Val Ala Pro  Met Leu Gln Ile Ile  Lys Ala Ala
            1010                1015                1020

Phe Met  Lys Pro Phe Ile Asp  Thr Leu Glu Ser Val  His Leu Ile
            1025                1030                1035

Tyr Ala  Ala Glu Asp Val Thr  Glu Leu Thr Tyr Arg  Glu Val Leu
            1040                1045                1050

Glu Glu  Arg Arg Arg Glu Ser  Arg Gly Lys Phe Lys  Lys Thr Phe
            1055                1060                1065

Val Leu  Asn Arg Pro Pro  Leu Trp Thr Asp Gly  Val Gly Phe
            1070                1075                1080

Ile Asp  Arg Gly Ile Leu Thr  Asn His Val Gln Pro  Pro Ser Asp
            1085                1090                1095

Asn Leu  Leu Val Ala Ile Cys  Gly Pro Pro Val Met  Gln Arg Ile
            1100                1105                1110

Val Lys  Ala Thr Leu Lys Thr  Leu Gly Tyr Asn Met  Asn Leu Val
            1115                1120                1125
```

Arg Thr Val Asp Glu Thr Glu Pro Ser Gly Ser
    1130                1135

<210> SEQ ID NO 8
<211> LENGTH: 472
<212> TYPE: PRT
<213> ORGANISM: Artificial Sequence
<220> FEATURE:
<223> OTHER INFORMATION: Rhizopus oryzae fumarase amino acid sequence,
      lacking the first 23 N-terminal amino acids.

<400> SEQUENCE: 8

Met Ser Ser Ala Ser Ala Ala Leu Gln Lys Phe Arg Ala Glu Arg Asp
1               5                   10                  15

Thr Phe Gly Asp Leu Gln Val Pro Ala Asp Arg Tyr Trp Gly Ala Gln
            20                  25                  30

Thr Gln Arg Ser Leu Gln Asn Phe Asp Ile Gly Gly Pro Thr Glu Arg
        35                  40                  45

Met Pro Glu Pro Leu Ile Arg Ala Phe Gly Val Leu Lys Lys Ala Ala
    50                  55                  60

Ala Thr Val Asn Met Thr Tyr Gly Leu Asp Pro Lys Val Gly Glu Ala
65                  70                  75                  80

Ile Gln Lys Ala Ala Asp Glu Val Ile Asp Gly Ser Leu Ile Asp His
                85                  90                  95

Phe Pro Leu Val Val Trp Gln Thr Gly Ser Gly Thr Gln Thr Lys Met
            100                 105                 110

Asn Val Asn Glu Val Ile Ser Asn Arg Ala Ile Glu Leu Leu Gly Gly
        115                 120                 125

Glu Leu Gly Ser Lys Ala Pro Val His Pro Asn Asp His Val Asn Met
    130                 135                 140

Ser Gln Ser Ser Asn Asp Thr Phe Pro Thr Ala Met His Val Ala Ala
145                 150                 155                 160

Val Val Glu Ile His Gly Arg Leu Ile Pro Ala Leu Thr Thr Leu Arg
                165                 170                 175

Asp Ala Leu Gln Ala Lys Ser Ala Glu Phe Glu His Ile Ile Lys Ile
            180                 185                 190

Gly Arg Thr His Leu Gln Asp Ala Thr Pro Leu Thr Leu Gly Gln Glu
        195                 200                 205

Phe Ser Gly Tyr Thr Gln Gln Leu Thr Tyr Gly Ile Ala Arg Val Gln
    210                 215                 220

Gly Thr Leu Glu Arg Leu Tyr Asn Leu Ala Gln Gly Gly Thr Ala Val
225                 230                 235                 240

Gly Thr Gly Leu Asn Thr Arg Lys Gly Phe Asp Ala Lys Val Ala Glu
                245                 250                 255

Ala Ile Ala Ser Ile Thr Gly Leu Pro Phe Lys Thr Ala Pro Asn Lys
            260                 265                 270

Phe Glu Ala Leu Ala Ala His Asp Ala Leu Val Glu Ala His Gly Ala
        275                 280                 285

Leu Asn Thr Val Ala Cys Ser Leu Met Lys Ile Ala Asn Asp Ile Arg
    290                 295                 300

Tyr Leu Gly Ser Gly Pro Arg Cys Gly Leu Gly Glu Leu Ser Leu Pro
305                 310                 315                 320

Glu Asn Glu Pro Gly Ser Ser Ile Met Pro Gly Lys Val Asn Pro Thr
                325                 330                 335

Gln Cys Glu Ala Met Thr Met Val Cys Ala Gln Val Met Gly Asn Asn

```
                   340                 345                 350
Thr Ala Ile Ser Val Ala Gly Ser Asn Gly Gln Phe Glu Leu Asn Val
            355                 360                 365

Phe Lys Pro Val Met Ile Lys Asn Leu Ile Gln Ser Ile Arg Leu Ile
            370                 375                 380

Ser Asp Ala Ser Ile Ser Phe Thr Lys Asn Cys Val Val Gly Ile Glu
385                 390                 395                 400

Ala Asn Glu Lys Lys Ile Ser Ser Ile Met Asn Glu Ser Leu Met Leu
            405                 410                 415

Val Thr Ala Leu Asn Pro His Ile Gly Tyr Asp Lys Ala Ala Lys Cys
            420                 425                 430

Ala Lys Lys Ala His Lys Glu Gly Thr Thr Leu Lys Glu Ala Ala Leu
            435                 440                 445

Ser Leu Gly Tyr Leu Thr Ser Glu Glu Phe Asp Gln Trp Val Arg Pro
            450                 455                 460

Glu Asp Met Ile Ser Ala Lys Asp
465                 470

<210> SEQ ID NO 9
<211> LENGTH: 340
<212> TYPE: PRT
<213> ORGANISM: Artificial Sequence
<220> FEATURE:
<223> OTHER INFORMATION: Saccharomyces cerevisiae peroxisomal malate
      dehydrogenase (Mdh3) amino acid sequence, lacking the 3 C-terminal
      peroxisomal targeting sequence (SKL).

<400> SEQUENCE: 9

Met Val Lys Val Ala Ile Leu Gly Ala Ser Gly Gly Val Gly Gln Pro
1               5                   10                  15

Leu Ser Leu Leu Leu Lys Leu Ser Pro Tyr Val Ser Glu Leu Ala Leu
            20                  25                  30

Tyr Asp Ile Arg Ala Ala Glu Gly Ile Gly Lys Asp Leu Ser His Ile
            35                  40                  45

Asn Thr Asn Ser Ser Cys Val Gly Tyr Asp Lys Asp Ser Ile Glu Asn
50                  55                  60

Thr Leu Ser Asn Ala Gln Val Val Leu Ile Pro Ala Gly Val Pro Arg
65                  70                  75                  80

Lys Pro Gly Leu Thr Arg Asp Asp Leu Phe Lys Met Asn Ala Gly Ile
            85                  90                  95

Val Lys Ser Leu Val Thr Ala Val Gly Lys Phe Ala Pro Asn Ala Arg
            100                 105                 110

Ile Leu Val Ile Ser Asn Pro Val Asn Ser Leu Val Pro Ile Ala Val
            115                 120                 125

Glu Thr Leu Lys Lys Met Gly Lys Phe Lys Pro Gly Asn Val Met Gly
            130                 135                 140

Val Thr Asn Leu Asp Leu Val Arg Ala Glu Thr Phe Leu Val Asp Tyr
145                 150                 155                 160

Leu Met Leu Lys Asn Pro Lys Ile Gly Gln Glu Gln Asp Lys Thr Thr
            165                 170                 175

Met His Arg Lys Val Thr Val Ile Gly Gly His Ser Gly Glu Thr Ile
            180                 185                 190

Ile Pro Ile Ile Thr Asp Lys Ser Leu Val Phe Gln Leu Asp Lys Gln
            195                 200                 205

Tyr Glu His Phe Ile His Arg Val Gln Phe Gly Gly Asp Glu Ile Val
            210                 215                 220
```

```
Lys Ala Lys Gln Gly Ala Gly Ser Ala Thr Leu Ser Met Ala Phe Ala
225                 230                 235                 240

Gly Ala Lys Phe Ala Glu Glu Val Leu Arg Ser Phe His Asn Glu Lys
            245                 250                 255

Pro Glu Thr Glu Ser Leu Ser Ala Phe Val Tyr Leu Pro Gly Leu Lys
            260                 265                 270

Asn Gly Lys Lys Ala Gln Gln Leu Val Gly Asp Asn Ser Ile Glu Tyr
            275                 280                 285

Phe Ser Leu Pro Ile Val Leu Arg Asn Gly Ser Val Val Ser Ile Asp
290                 295                 300

Thr Ser Val Leu Glu Lys Leu Ser Pro Arg Glu Glu Gln Leu Val Asn
305                 310                 315                 320

Thr Ala Val Lys Glu Leu Arg Lys Asn Ile Glu Lys Gly Lys Ser Phe
            325                 330                 335

Ile Leu Asp Ser
            340

<210> SEQ ID NO 10
<211> LENGTH: 438
<212> TYPE: PRT
<213> ORGANISM: Schizosaccharomyces pombe
<220> FEATURE:
<223> OTHER INFORMATION: malate permease amino acid sequence

<400> SEQUENCE: 10

Met Gly Glu Leu Lys Glu Ile Leu Lys Gln Arg Tyr His Glu Leu Leu
1               5                   10                  15

Asp Trp Asn Val Lys Ala Pro His Val Pro Leu Ser Gln Arg Leu Lys
            20                  25                  30

His Phe Thr Trp Ser Trp Phe Ala Cys Thr Met Ala Thr Gly Gly Val
        35                  40                  45

Gly Leu Ile Ile Gly Ser Phe Pro Phe Arg Phe Tyr Gly Leu Asn Thr
    50                  55                  60

Ile Gly Lys Ile Val Tyr Ile Leu Gln Ile Phe Leu Phe Ser Leu Phe
65                  70                  75                  80

Gly Ser Cys Met Leu Phe Arg Phe Ile Lys Tyr Pro Ser Thr Ile Lys
                85                  90                  95

Asp Ser Trp Asn His His Leu Glu Lys Leu Phe Ile Ala Thr Cys Leu
            100                 105                 110

Leu Ser Ile Ser Thr Phe Ile Asp Met Leu Ala Ile Tyr Ala Tyr Pro
        115                 120                 125

Asp Thr Gly Glu Trp Met Val Trp Val Ile Arg Ile Leu Tyr Tyr Ile
    130                 135                 140

Tyr Val Ala Val Ser Phe Ile Tyr Cys Val Met Ala Phe Phe Thr Ile
145                 150                 155                 160

Phe Asn Asn His Val Tyr Thr Ile Glu Thr Ala Ser Pro Ala Trp Ile
                165                 170                 175

Leu Pro Ile Phe Pro Pro Met Ile Cys Gly Val Ile Ala Gly Ala Val
            180                 185                 190

Asn Ser Thr Gln Pro Ala His Gln Leu Lys Asn Met Val Ile Phe Gly
        195                 200                 205

Ile Leu Phe Gln Gly Leu Gly Phe Trp Val Tyr Leu Leu Leu Phe Ala
    210                 215                 220

Val Asn Val Leu Arg Phe Phe Thr Val Gly Leu Ala Lys Pro Gln Asp
225                 230                 235                 240
```

-continued

```
Arg Pro Gly Met Phe Met Phe Val Gly Pro Pro Ala Phe Ser Gly Leu
            245             250             255
Ala Leu Ile Asn Ile Ala Arg Gly Ala Met Gly Ser Arg Pro Tyr Ile
            260             265             270
Phe Val Gly Ala Asn Ser Ser Glu Tyr Leu Gly Phe Val Ser Thr Phe
        275             280             285
Met Ala Ile Phe Ile Trp Gly Leu Ala Ala Trp Cys Tyr Cys Leu Ala
    290             295             300
Met Val Ser Phe Leu Ala Gly Phe Phe Thr Arg Ala Pro Leu Lys Phe
305             310             315                         320
Ala Cys Gly Trp Phe Ala Phe Ile Phe Pro Asn Val Gly Phe Val Asn
            325             330             335
Cys Thr Ile Glu Ile Gly Lys Met Ile Asp Ser Lys Ala Phe Gln Met
            340             345             350
Phe Gly His Ile Ile Gly Val Ile Leu Cys Ile Gln Trp Ile Leu Leu
            355             360             365
Met Tyr Leu Met Val Arg Ala Phe Leu Val Asn Asp Leu Cys Tyr Pro
    370             375             380
Gly Lys Asp Glu Asp Ala His Pro Pro Lys Pro Asn Thr Gly Val
385             390             395             400
Leu Asn Pro Thr Phe Pro Pro Glu Lys Ala Pro Ala Ser Leu Glu Lys
            405             410             415
Val Asp Thr His Val Thr Ser Thr Gly Gly Glu Ser Asp Pro Pro Ser
            420             425             430
Ser Glu His Glu Ser Val
            435
```

DICARBOXYLIC ACID PRODUCTION BY FERMENTATION AT LOW PH

This application is the U.S. national phase of International Application No. PCT/EP2009/056181 filed 20 May 2009, which designated the U.S. and claims priority to EP Application No. 08159891.4, filed 8 Jul. 2008, the entire contents of each of which are hereby incorporated by reference.

FIELD OF THE INVENTION

The present invention relates to a process for the production of dicarboxylic acids. In particular, it relates to the production of dicarboxylic acids by fermentation of a yeast.

BACKGROUND OF THE INVENTION

Dicarboxylic acids, such as fumaric acid and succinic acid, are important compounds which are used in the food industry for the preparation and preservation of food, in the medical industry for the formulation of medical products and other industrial uses, such as monomers for (bio)polymers. To meet the increasing need for dicarboxylic acids, more efficient and cost effective production methods are being developed. Traditionally, dicarboxylic acids are made by fermentation of bacteria, which can produce large amounts of dicarboxylic acids. This is for example described in U.S. Pat. No. 5,573,931 which describes a method for producing succinic acid in high concentrations by employing a bacterial strain. However, one major drawback associated with the use of bacteria for producing dicarboxylic acids is the formation of dicarboxylic acid salt. If bacteria are used, the pH during fermentation needs to be maintained in the range of pH 6-7, which is higher than the pKa values of all dicarboxylic acids. As a consequence, most acids will be produced in their salt form and the salts will have to be converted into the acid. This is not practical or efficient in large-scale production processes and raises production costs. Also microorganisms other than bacteria have been employed for the production of organic acids. EP 0 424 384 discloses an aerobic process for the production of organic acids by *Rhizopus* in a medium containing calcium carbonate. EP 1 183 385 discloses genetically manipulated yeast cells with a Crabtree negative phenotype and containing an exogenous nucleus acid molecule for the production of lactic acid.

DETAILED DESCRIPTION

The present invention relates to a process for the production of a dicarboxylic acid. The process comprises fermenting a yeast in the presence of a carbohydrate-containing substrate and low amounts of oxygen at a pH value which is below the pKa of the dicarboxylic acid. The process of the present invention allows for high yields of the dicarboxylic acid product, allows for a simpler downstream processing and is more cost-effective than existing processes in which the salt is produced which has then to be converted to the acid. Since dicarboxylic acids have more than one pKa value, the pH should be below the lowest pKa of the dicarboxylic acid. For most acids, the pH will typically be in the range of pH 1.0 to pH 5.5, preferably between pH 2.0 and pH 4.0. In one embodiment, succinic acid is produced at a pH value of 3.0. Another advantage is that due to the low pH the risk of contamination is reduced.

The acid production phase is preferably preceded by a biomass formation phase for optimal biomass production. In the biomass formation phase the pH is in the range of pH 2 to pH 7. Preferably, the pH is in the range of pH 3 to pH 6, more preferably, the pH is in the range of pH 4 to pH 5.

The process according to the present invention is more cost-effective and may lead to a 30% lower cost price. One of the reasons is that titrant costs are significantly reduced.

The process may be used for the production of any dicarboxylic acid. Suitable examples include adipic acid, fumaric acid, itaconic acid, succinic acid, malic acid, oxalic acid. Preferably, the dicarboxylic acid is succinic acid, fumaric acid or malic acid.

The yeast which is used in the process may be any suitable yeast. Suitable examples of yeasts include *Saccharomyces, Schizosaccharomyces, Kluyveromyces, Candida, Pichia* and *Yarrowia*, such as species of *Saccharomyces cerevisiae, Schizosaccharomyces pombe, Kluyvermoces lactis, Candida sonorensis, Pichia stipidis* and *Yarrowia lipolytica*. In one embodiment, the eukaryotic microorganism used in the process is a *Saccharomyces cerevisiae*, a microorganism which is a widely used industrially interesting microorganism.

In a preferred embodiment the yeast according to the present invention is a genetically modified yeast. As used herein, a genetically modified yeast in the process according to the present invention is defined as a yeast cell which contains, or is transformed or genetically modified with a nucleotide sequence or polypeptide that does not naturally occur in the yeast cell, or it contains additional copy or copies of an endogenous nucleic acid sequence. A wild-type yeast cell is herein defined as the parental cell of the recombinant cell.

Preferably, the yeast in the process according to the present invention is a genetically modified yeast comprising a nucleotide sequence encoding a heterologous enzyme selected from the group consisting of a phosphoenolpyruvate carboxykinase, fumarate reductase and a fumarase. Preferred embodiments of the heterologous enzymes are as defined herein below.

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain.

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but have been obtained from another cell or synthetically or recombinantly produced.

Preferably the genetically modified yeast comprises a nucleotide sequence encoding a phosphoenolpyruvate carboxykinase. The PEP carboxykinase (EC 4.1.1.49) preferably is a heterologous enzyme, preferably derived from bacteria, more preferably the enzyme having PEP carboxykinase activity is derived from *Escherichia coli, Mannheimia* sp., *Actinobacillus* sp., or *Anaerobiospirillum* sp., more preferably *Mannheimia succiniciproducens* or *Actinobacillus succinogenes*. In one embodiment the PEP carboxykinase is derived from *Actinobacillus succinogenes* (PCKa), wherein the PCKa preferably has been modified to replace EGY at position 120-122 with a DAF amino acid sequence. Preferably, a yeast cell according to the present invention is genetically modified with a PEP carboxykinase which has at least 80, 85, 90, 95, 99 or 100% sequence identity with amino acid sequence of SEQ ID NO: 6.

In another preferred embodiment a genetically modified yeast in the process according to the present invention comprises a nucleotide sequence encoding a fumarate reductase. Preferably, the fumarate reductase is a heterologous enzyme, preferably a NAD(H)-dependent fumarate reductase, which may be derived from any suitable origin, for instance bacteria, fungi, protozoa or plants. Preferably, a yeast in the process according to the invention comprises a heterologous NAD(H)-dependent fumarate reductase, preferably derived from a *Trypanosoma* sp., for instance a *Trypanosoma brucei*. In a preferred embodiment the nucleotide sequence encoding a NAD(H)-dependent fumarate reductase is expressed in the cytosol. In the event that the nucleotide sequence encoding a NAD(H)-dependent fumarate reductase comprises a peroxisomal or mitochondrial targeting signal, it may be essential to modify or delete a number of amino acids (and corresponding nucleotide sequences in the encoding nucleotide sequence) in order to prevent peroxisomal or mitochondrial targeting of the enzyme. The presence of a peroxisomal targeting signal may for instance be determined by the method disclosed by Schlüter et al, Nucleic acid Research 2007, 35, D815-D822. Preferably, a yeast cell according to the present invention is genetically modified with a NAD(H)-dependent fumarate reductase, which has at least 80, 85, 90, 95, 99 or 100% sequence identity with SEQ ID NO: 7.

In another preferred embodiment a genetically modified yeast in the process according to the present invention comprises a nucleotide sequence encoding a fumarase, which may be a heterologous or homologous enzyme. A nucleotide sequence encoding a heterologous fumarase may be derived from any suitable origin, preferably from microbial origin, preferably from a yeast, for instance *Saccharomyces cerevisiae* or a filamentous fungus, for instance *Rhizopus oryzae*. Preferably, a yeast in the process according to the present invention overexpresses a nucleotide sequence encoding a fumarase that has at least 70%, preferably at least 75, 80, 85, 90, 92, 94, 95, 96, 97, 98, or 99% or 100% sequence identity with the amino acid sequence of SEQ ID NO: 8.

In another preferred embodiment a genetically modified yeast in the process according to the present invention further comprises a nucleotide sequence encoding a malate dehydrogenase (MDH) which is active in the cytosol upon expression of the nucleotide sequence. Preferably, the MDH lacks a peroxisomal or mitochondrial targeting signal in order to localize the enzyme in the cytosol. A cytosolic MDH may be any suitable homologous or heterologous malate dehydrogenase. Preferably, a yeast cell according to the present invention comprises a nucleotide sequence encoding a malate dehydrogenase that has at least 70%, preferably at least 75, 80, 85, 90, 92, 94, 95, 96, 97, 98, 99% sequence identity with the amino acid sequence of SEQ ID NO: 9.

In another embodiment, a genetically modified yeast in the process according to the invention comprises a nucleotide sequence encoding a dicarboxylic acid transporter protein, preferably a malic acid transporter protein (MAE). A dicarboxylic acid transporter protein may be a homologous or heterologous protein. Preferably the dicarboxylic acid transporter protein is a heterologous protein. A dicarboxylic acid transporter protein may be derived from any suitable organism, preferably from *Schizosaccharomyces pombe*. Preferably, a dicarboxylic acid transporter protein is a malic acid transporter protein (MAE) which has at least 80, 85, 90, 95 or 99% or 100% sequence identity with SEQ ID NO: 10.

Preferably, the yeast used in the process according to the present invention is a genetically modified yeast comprising a heterologous PEP-carboxykinase, a heterologous NAD(P)H-dependent fumarate reductase, a heterologous fumarase, a heterologous malic acid transporter protein and a cytosolic malate dehydrogenase. Preferred embodiments of these enzymes are as defined herein above.

Sequence identity is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences.

Preferred methods to determine identity are designed to give the largest match between the sequences tested. Methods to determine identity and similarity are codified in publicly available computer programs. Preferred computer program methods to determine identity and similarity between two sequences include BLASTP and BLASTN, publicly available from NCBI and other sources (BLAST Manual, Altschul, S., et al., NCBI NLM NIH Bethesda, Md. 20894). Preferred parameters for amino acid sequences comparison using BLASTP are gap open 11.0, gap extend 1, Blosum 62 matrix.

The term "nucleic acid" as used herein, includes reference to a deoxyribonucleotide or ribonucleotide polymer, i.e. a polynucleotide, in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). A polynucleotide can be full-length or a subsequence of a native or heterologous structural or regulatory gene. Unless otherwise indicated, the term includes reference to the specified sequence as well as the complementary sequence thereof.

In a preferred embodiment, the yeast in the process according to the invention overexpresses the nucleotide sequences encoding any of the enzymes as defined herein above. There are various means available in the art for overexpression of nucleotide sequences encoding enzymes in a yeast in the process of the invention. In particular, a nucleotide sequence encoding an enzyme may be overexpressed by increasing the copy number of the gene coding for the enzyme in the cell, e.g. by integrating additional copies of the gene in the cell's genome, by expressing the gene from a centromeric vector, from an episomal multicopy expression vector or by introducing an (episomal) expression vector that comprises multiple copies of the gene. Preferably, overexpression of the enzyme according to the invention is achieved with a (strong) constitutive promoter.

The carbohydrate-containing substrate may be any carbohydrate containing substrate including molasses, sugar cane juice, pentoses and hexoses, such as glucose, fructose, xylose, arabinose. Preferably, the carbohydrate-containing substrate is a glucose-containing substrate, such as maltose, sucrose, glucose or a glucose syrup. The carbohydrate content of the carbohydrate-containing substrate is preferably more than 50% w/w, more preferably more than 55%, 60%, 65%, 70%, 75%, 80% w/w, most preferably more than 85%, 90%, 95% or 99% w/w on the basis of dry matter content.

The process according to the present invention, preferably comprises fermenting a yeast under carbon (C)-limited conditions. C-limited conditions are defined herein as a concentration of dissolved carbohydrate of below 1 g/l, preferably below 0.9 g/l, 0.8 or below 0.5 g/l of dissolved carbohydrate.

It was found that fermenting yeast under C-limited conditions resulted in an increased yield of succinic acid as compared to non-C-limited conditions.

The oxygen for the fermentation may be supplied in any suitable form. In one embodiment, the oxygen is supplied in the form of air. The oxygen should be supplied in low amounts. This is reflected in the oxygen uptake rate (OUR) and/or the specific oxygen uptake rate ($qO_2$) of the yeast. The OUR in the present invention is lower than about 8.0 mmol oxygen/L/hour, preferably lower than about 5.0, 4.0, 3.0, or 2.0 mmol oxygen/L/hour, more preferably lower than about 1.0, or 0.5 mmol oxygen/L/hour, preferably above 0.01 mmol oxygen/L/hour.

The specific oxygen uptake rate ($qO_2$) in the process of the invention ranges between 8 mmol oxygen/g biomass dry weight/hour to 0.5 mmol oxygen/g biomass dry weight/hour, preferably between 5, 4, 3, or 2 mmol oxygen/g biomass/hour to about 0.4, 0.3, or 0.2 mmol/oxygen/g biomass/hour.

The process according to the present invention may be carried out in batch, fed-batch or continuous mode. These fermentation modes are known to the skilled man in the art. Depending on the fermentation mode, the biomass concentration during fermentation may vary more or less during fermentation. In batch and fed-batch mode the biomass concentration usually increases. Consequently, the specific oxygen uptake rate usually decreases in a batch and fed-batch mode.

The temperature of the process is typically between 10 and 40 degrees C., preferably between 20 and 35 degrees C., more preferably between 30 and 35 degrees C.

In one embodiment of the process according to the invention, an extra electron donor is present in addition to the carbohydrate-containing substrate. The extra electron donor is preferably an organic electron donor. Suitable examples of organic electron donors include glycerol, formate and polyols, such as mannitol, sorbitol and xylitol.

FIGURES

FIG. 1. Effect of the applied OUR on the succinic acid production after 90 h at pH 3.

EXAMPLES

Example 1

Succinic Acid Production by *Saccharomyces cerevisiae*

1.1. Construction Yeast Strain
1.1.1. Construction of Expression Constructs

Expression construct pGBS414PPK-3 was created after a BamHI/NotI restriction of the *S. cerevisiae* expression vector pRS414 (Sirkoski R. S, and Hieter P, Genetics, 1989, 122(1): 19-27) and subsequently ligating in this vector a BamHI/NotI restriction fragment consisting of the phosphoenolpyruvate carboxykinase (origin *Actinobacillus succinogenes*) synthetic gene construct (SEQ ID NO: 1). The ligation mix was used for transformation of *E. coli* TOP10 (Invitrogen) resulting in the yeast expression construct pGBS414PPK-1. Subsequently, pGBK414PPK-1 was restricted with AscI and NotI. To create pGBS414PPK-3, an AscI/NotI restriction fragment consisting of glycosomal fumarate reductase from *T. brucei* (FRDg) synthetic gene construct (SEQ ID NO: 2) was ligated into the restricted pGBS414PPK-1 vector. The ligation mix was used for transformation of *E. coli* TOP10 (Invitrogen) resulting in the yeast expression construct pGBS414PPK-3.

The expression construct pGBS415FUM-3 was created after a BamHI/NotI restriction of the *S. cerevisiae* expression vector pRS415 (Sirkoski R. S, and Hieter P, Genetics, 1989, 122(1):19-27) and subsequently ligating in this vector a BamHI/NotI restriction fragment consisting of the fumarase (origin *Rhizopus oryzae*) synthetic gene construct (SEQ ID NO: 3). The ligation mix was used for transformation of *E. coli* TOP10 (Invitrogen) resulting in the yeast expression construct pGBS415FUM-1. Subsequently, pGBK415FUM-1 was restricted with AscI and NotI. To create pGBS415FUM-3, an AscI/NotI restriction fragment consisting of peroxisomal malate dehydrogenase from *S. cerevisiae* (MDH3) synthetic gene construct (SEQ ID NO: 4) was ligated into the restricted pGBS415FUM-1 vector. The ligation mix was used for transformation of *E. coli* TOP10 (Invitrogen) resulting in the yeast expression construct pGBS415FUM-3.

The expression construct pGBS416MAE-1 was created after a BamHI/NotI restriction of the *S. cerevisiae* expression vector pRS416 (Sirkoski R. S, and Hieter P, Genetics, 1989, 122(1):19-27) and subsequently ligating in this vector a BamHI/NotI restriction fragment consisting of the *Schizosaccharomyces pombe* malate transporter synthetic gene construct (SEQ ID NO: 5). The ligation mix was used for transformation of *E. coli* TOP10 (Invitrogen) resulting in the yeast expression construct pGBS416MAE-1.

1.1.2. Construction *S. cerevisiae* Strain

Plasmids pGBS414PPK-3, pGBS415FUM-3 and pGBS416MAE-1 (described under 1.1.) were transformed by electroporation into *S. cerevisiae* strain RWB064 (MATA ura3-52 leu2-112 trp1-289 adh1::lox adh2::lox gpd1::Kanlox) to create strain SUC-200, overexpressing PCKa, MDH3, FUMR, FRDg and SpMAE1. All genes were codon pair optimized for expression in *S. cerevisiae* according to WO2008/000632.

1.2. Succinic Acid Production *S. Cerevisiae* at Low pH and Oxygen Limited Conditions The yeast strain SUC-200 (MATA ura3-52 leu2-112 trp1-289 adh1::lox adh2::lox gpd1::Kanlox, overexpressing PCKa, MDH3, FUMR, FRDg and SpMAE1), was cultivated in shake-flask (2×300 ml) for 3 days at 30° C. and 220 rpm. The medium was based on Verduyn (Verduyn et. al., 1992, Yeast 8, 501-517), but modifications in carbon and nitrogen source were made as shown in Table 1.

TABLE 1

Preculture shake flask medium composition

| Compound | Concentration (g/l) |
|---|---|
| $C_6H_{12}O_6 \cdot H_2O$ | 20.0 |
| $(NH_2)_2CO$ | 2.3 |
| $KH_2PO_4$ | 3.0 |
| $MgSO_4 \cdot 7H_2O$ | 0.5 |
|  | 1 |
|  | 1 |

| <sup>a</sup>Vitamin solution | | |
|---|---|---|
| Component | Formula | Concentration (g/kg) |
| Biotin (D-) | $C_{10}H_{16}N_2O_3S$ | 0.05 |
| Ca D(+) panthothenate | $C_{18}H_{32}CaN_2O_{10}$ | 1.00 |
| Nicotinic acid | $C_6H_5NO_2$ | 1.00 |
| Myo-inositol | $C_6H_{12}O_6$ | 25.00 |

TABLE 1-continued

| | | |
|---|---|---|
| Thiamine chloride hydrochloride | $C_{12}H_{18}Cl_2N_4OS \cdot xH_2O$ | 1.00 |
| Pyridoxol hydrochloride | $C_8H_{12}ClNO_3$ | 1.00 |
| p-aminobenzoic acid | $C_7H_7NO_2$ | 0.20 |

[b]Trace elements solution

| Formula | Concentration (g/kg) |
|---|---|
| $C_{10}H_{14}N_2Na_2O_8 \cdot 2H_2O$ (EDTA) | 15.00 |
| $ZnSO_4 \cdot 7H_2O$ | 4.50 |
| $MnCl_2 \cdot 2H_2O$ | 0.84 |
| $CoCl_2 \cdot 6H_2O$ | 0.30 |
| $CuSO_4 \cdot 5H_2O$ | 0.30 |
| $Na_2MoO_4 \cdot 2H_2O$ | 0.40 |
| $CaCl_2 \cdot 2H_2O$ | 4.50 |
| $FeSO_4 \cdot 7H_2O$ | 3.00 |
| $H_3BO_3$ | 1.00 |
| KI | 0.10 |

Subsequently, the content of the shake-flasks was transferred to 10 L fermenter (Startweight 6 kg), which contained the following medium:

TABLE 2

Main fermentation medium composition

| Raw material | Formula | Concentration (g/l) |
|---|---|---|
| Ammonium sulphate | $(NH_4)_2SO_4$ | 2.5 |
| Potassium dihydrogen phosphate | $KH_2PO_4$ | 3.0 |

TABLE 2-continued

Main fermentation medium composition

| Raw material | Formula | Concentration (g/l) |
|---|---|---|
| Magnesium sulphate | $MgSO_4 \cdot 7H_2O$ | 0.5 |
| Trace element solution | | 1 |
| Vitamin solution | | 1 |

The pH was controlled at 3.0 by addition of 6 N KOH. The temperature was controlled at 30° C. Glucose concentration was kept limited (<1 g/l) by controlling feed addition to the fermenter. Different oxygen uptake rates (OUR) were applied to the fermentation, which resulted in oxygen limitation (FIG. 1).

0.33 vvm of total gasflow was applied, including 10% $CO_2$ to supply enough $CO_2$ for efficient succinic acid production.

The results of different applied OUR's on the succinic acid production are shown in FIG. 1. A minimal amount of aeration was required to sustain succinic acid production at a pH of 3. An OUR above 5 mmol/L/h resulted in lower succinic acid production.

During the cultivation of 90 hours, growth occurred to a typical biomass concentration of 8 g dry weight/L. Consequently, the specific oxygen uptake rate ($qO_2$) decreased constantly during the fermentation. An OUR of 10 mmol/L/h applied in one fermentation correlated with a $qO_2$ decreasing from 10 to 1.25 mmol/g biomass dry weight/h and an OUR of 1 mmol/L/h correlated with a $qO_2$ decreasing from 1 to 0.1 mmol/g biomass dry weight/h.

The invention claimed is:

1. A process for the preparation of succinic acid, comprising: fermenting a yeast in the presence of a carbohydrate-containing substrate and low amounts of oxygen at a pH value which is below the lowest pKa of the succinic acid, wherein the oxygen is supplied at a specific oxygen uptake rate ranging from 8 to 0.2 mmol oxygen/g biomass dry weight/hour, and wherein, in an acid production phase, said process produces more than 10 g/L succinic acid during cultivation for 90 hours.

2. The process according to claim 1, wherein the pH is in the range of pH 1.0 to pH 5.5.

3. The process according to claim 1, comprising fermenting yeast under carbon-limited conditions.

4. The process according to claim 1, wherein the process is carried out in the presence of an extra electron donor.

5. The process according to claim 1, wherein the yeast is a *Saccharomyces cerevisiae*.

6. The process according to claim 1, wherein the yeast is a genetically modified yeast.

7. The process according to claim 6, wherein the genetically modified yeast comprises a nucleotide sequence encoding a heterologous enzyme selected from the group consisting of a phosphoenol pyruvate carboxykinase, fumarate reductase and a fumarase.

8. The process according to claim 1, wherein the pH is in the range of pH 2.0 to pH 4.0.

9. The process according to claim 1, wherein the pH is 3.0.

10. The process according to claim 1, wherein the oxygen is supplied at a specific oxygen uptake rate ranging from 5 to 0.2 mmol oxygen/g biomass dry weight/hour.

11. The process according to claim 3, wherein the carbon-limited conditions comprise a dissolved carbohydrate concentration below 1 g/l.

12. The process according to claim 3, wherein the carbon-limited conditions comprise a dissolved carbohydrate concentration below 0.5 g/l.

13. The process according to claim 4, wherein the extra electron donor is an organic electron donor.

14. The process according to claim 1 which produces more than 12 g/L succinic acid during cultivation for 90 hours.

* * * * *